US012769943B2

(12) United States Patent
Xu et al.

(10) Patent No.: US 12,769,943 B2
(45) Date of Patent: Oct. 20, 2026

(54) SYSTEM, METHOD AND STORAGE MEDIUM FOR EXTRACTING TARGETED MEDICAL INFORMATION FROM CLINICAL NOTES

(71) Applicant: KONINKLIJKE PHILIPS N.V., Eindhoven (NL)

(72) Inventors: Dongfang Xu, Cambridge, MA (US); Ankur Sukhalal Padia, Cambridge, MA (US); Kathy Mi Young Lee, Cambridge, MA (US); Vadiraj Hombal, Cambridge, MA (US); Vivek Varma Datla, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 213 days.

(21) Appl. No.: 18/231,484

(22) Filed: Aug. 8, 2023

(65) Prior Publication Data

US 2024/0062005 A1 Feb. 22, 2024

Related U.S. Application Data

(60) Provisional application No. 63/399,237, filed on Aug. 19, 2022.

(51) Int. Cl.
*G06F 40/284* (2020.01)
*G06F 40/103* (2020.01)
(Continued)

(52) U.S. Cl.
CPC .......... *G06F 40/284* (2020.01); *G06F 40/103* (2020.01); *G06F 40/169* (2020.01); *G06F 40/177* (2020.01); *G16H 10/60* (2018.01)

(58) Field of Classification Search
CPC .... G06F 40/284; G06F 40/103; G06F 40/169; G06F 40/177; G06F 40/30; G16H 10/60
See application file for complete search history.

(56) References Cited

U.S. PATENT DOCUMENTS

2014/0330586 A1* 11/2014 Riskin .................... G16H 15/00 705/3
2015/0066537 A1* 3/2015 Sheffer .................. G16H 10/60 705/3

(Continued)

OTHER PUBLICATIONS

Britney Muller :"BERT 101 State of The Art NLP Model Explained" GitHub, Mar. 2, 2022 (Year: 2022).*

(Continued)

*Primary Examiner* — Darioush Agahi

(57) ABSTRACT

A system (100) is extracting targeted medical information from clinical notes stored in memory (120). The system (100) includes a preprocessing module (120*a*) configured to retrieve from the memory (120) a sequence of clinical texts of electronic health records, and to tokenize the sequence of clinical texts to obtain a sequence of input tokens. The system (100) further includes a sequence to structure model module (120*b*) configured to transform, using a trained natural language based transformer, the sequence of input tokens into a sequence of structured output tokens. The system (100) further includes a post-processing unit (110) configured to obtain annotated text-label pairs of the clinical texts from the structure output tokens.

16 Claims, 6 Drawing Sheets

(51) Int. Cl.

| | |
|---|---|
| ***G06F 40/169*** | (2020.01) |
| ***G06F 40/177*** | (2020.01) |
| ***G16H 10/60*** | (2018.01) |

(56) References Cited

U.S. PATENT DOCUMENTS

| | | | | |
|---|---|---|---|---|
| 2015/0173522 | A1* | 6/2015 | Manouchehri | A47C 21/044<br>5/423 |
| 2015/0356198 | A1* | 12/2015 | D'Souza | G16H 50/20<br>705/2 |
| 2015/0356260 | A1 | 12/2015 | Souza | |
| 2020/0279271 | A1* | 9/2020 | Gasperecz | G06N 5/01 |
| 2021/0343411 | A1 | 11/2021 | Zhang | |
| 2021/0350915 | A1* | 11/2021 | Letinic | G06F 40/30 |
| 2022/0319703 | A1* | 10/2022 | Etienne | G16H 20/10 |
| 2024/0347064 | A1* | 10/2024 | Li | G06N 3/045 |

OTHER PUBLICATIONS

International Search Report for PCT/EP2023/072713 filed Aug. 17, 2023.

* cited by examiner

SYSTEM, METHOD AND STORAGE MEDIUM FOR EXTRACTING TARGETED MEDICAL INFORMATION FROM CLINICAL NOTES

CROSS-REFERENCE TO RELATED APPLICATION(S)

A claim of priority is made to U.S. Provisional Application No. 63/399,237, filed Aug. 19, 2022, the disclosure of which is incorporated by reference herein in its entirety.

BACKGROUND

Social determinants of health (SDOH) are the conditions in which people live that affect quality-of-life and health outcomes. A wide range of conditions are encompassed by SDOH, such as substance use, living situation, employment, education, racism, geography, pollution, and so on. Understanding SDOH, including behaviors influenced by these social factors, can inform clinical decision-making. However, most detailed SDOH are characterized in the Electronic Health Record through unstructured clinical text. This text-encoded information must be automatically extracted for secondary use applications, like large-scale retrospective studies and clinical decision support systems.

Currently, most event extraction methods employ a decomposition strategy, i.e., decomposing the prediction of complex event structures into multiple separated subtasks (mostly including entity recognition, trigger detection, argument classification), and then compose the components of different subtasks for predicting the whole event structure (e.g., pipeline modeling, joint modeling or joint inference). One main drawback of these decomposition-based methods is the need for massive and fine-grained annotations for different subtasks, often resulting in a data inefficiency problem. For example, they require different fine-grained annotations for Employment trigger detection, for Employment type classification, for Employment status classification, etc. And typically, for each of these subtasks, an individual system is implemented to extract the corresponding annotations, which results in a very complex pipeline system.

Another drawback of decomposition-based methods is that it is very challenging to design the optimal composition architecture of different subtasks manually. For instance, the pipeline models often lead to error propagation. Further, the joint models need to heuristically predefine the information sharing and decision dependence between trigger detection, argument classification, and entity recognition, often resulting in suboptimal and inflexible architectures.

SUMMARY

According to an aspect of the inventive concepts, a computer-implemented method is provided for extracting targeted medical information from clinical notes stored in memory. The method includes retrieving from the memory a sequence of clinical texts of electronic health records, and tokenizing the sequence of clinical texts to obtain a sequence of input tokens. The method further includes transforming, using a trained natural language based transformer, the sequence of input tokens into a sequence of structured output tokens. The method still further includes post-processing the structured output tokens to obtain annotated text-label pairs of the clinical texts.

The natural language based transformer may be a T5 transformer. The T5 transformer may include an encoder that receives a sequence of as inputs, and generates a sequence of representations, and a decoder receives the sequence of representations and a previously generated token as inputs to generate one output token at each time step.

The post-processing may further include converting the text-label pairs into a table format.

The targeted medical information may be social determinants of health (SDOH) information.

According to another aspect of the inventive concepts, a system for extracting targeted medical information from clinical notes stored in memory is provided. The system includes a preprocessing module, a sequence to structure model module, and a post-processing module. The preprocessing module is configured to retrieve from the memory a sequence of clinical texts of electronic health records, and to tokenize the sequence of clinical texts to obtain a sequence of input tokens. The sequence to structure model module is configured to transform, using a trained natural language based transformer, the sequence of input tokens into a sequence of structured output tokens. The post-processing module is configured to obtain annotated text-label pairs of the clinical texts from the structure output tokens.

The natural language based transformer of the sequence to structure model module may be a T5 transformer. The T5 transformer may include an encoder that receives a sequence of as inputs, and generates a sequence of representation, and a decoder that receives the sequence of representations and a previously generated token as inputs to generate one output token at each time step.

The post-processing module may be further configured to convert the text-label pairs into a table format.

The targeted medical information may be social determinants of health (SDOH) information.

According to yet another aspect of the inventive concepts, a non-transitory computer readable computer medium is encoded with instructions that when executed extract targeted medical information form clinical notes stored in memory. The medium includes a preprocessing module that when executed retrieves from the memory a sequence of clinical texts of electronic health records, and tokenizes the sequence of clinical texts to obtain a sequence of input tokens. The medium further includes a sequence to structure model module that when executed transforms, using a trained natural language based transformer, the sequence of input tokens into a sequence of structured output tokens. The medium further includes a post-processing module that when executed obtains annotated text-label pairs of the clinical texts from the structure output tokens.

The natural language based transformer of the sequence to structure model module may be a T5 transformer. The T5 transformer may include an encoder that receives a sequence of as inputs, and generates a sequence of representation, and a decoder receives the sequence of representations and a previously generated token as inputs to generate one output token at each time step.

The post-processing module when executed may convert the text-label pairs into a table format.

The targeted medical information may be social determinants of health (SDOH) information.

BRIEF DESCRIPTION OF THE DRAWINGS

The above and other aspects and features of the inventive concepts will become readily understood from the detailed description that follows, with reference to the accompanying drawings, in which.

DETAILED DESCRIPTION

Figure 1:
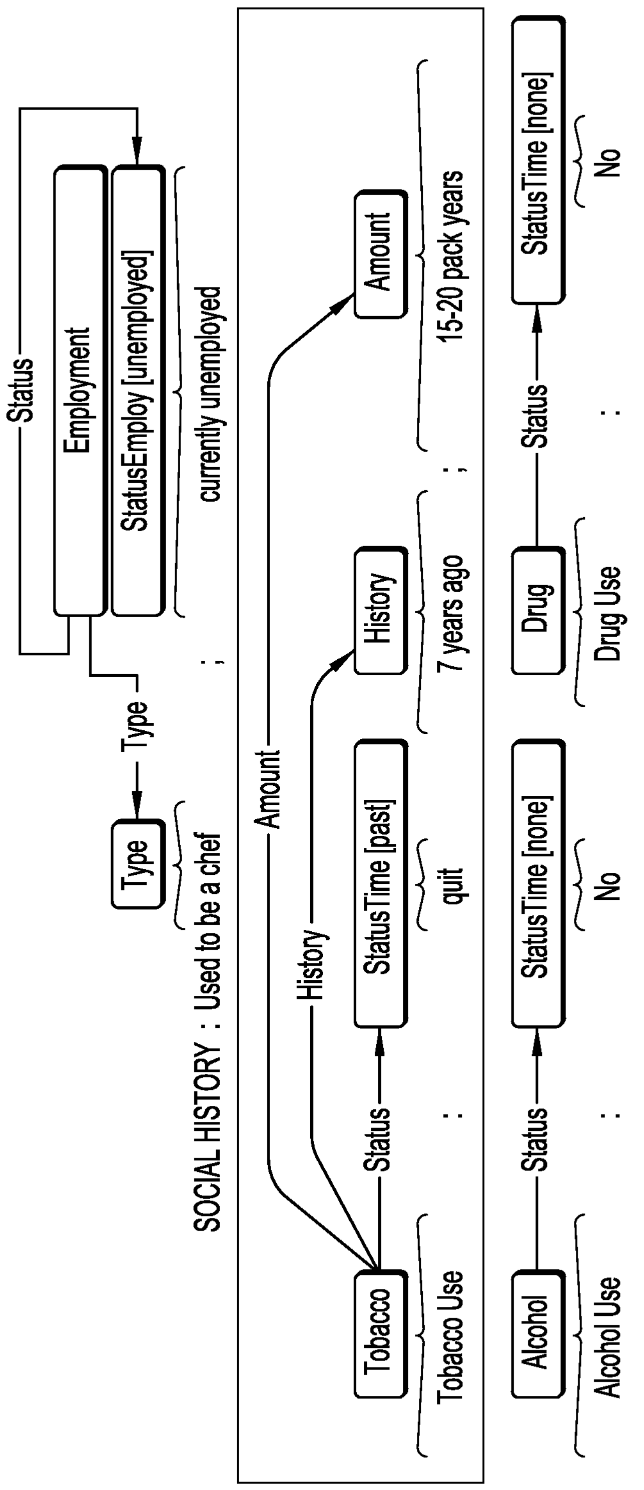
FIG. 1 illustrates an example of SDOH annotations in BRAT format.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

An Electronic Health Record (EHR) generally refers to a digital version of a patient's paper chart. EHRs are real-time, patient-centered records that make information available instantly and securely to authorized users. While an EHR does contain the medical and treatment histories of patients, an EHR system is built to go beyond standard clinical data collected in a provider's office and can be inclusive of a broader view of a patient's care. EHRs are a vital part of health information technology, and among other benefits, allow access to evidence-based tools that providers can use to make decisions about a patient's care. One of the key features of an EHR is that health information can be created and managed by authorized providers in a digital format capable of being shared with other providers across more than one health care organization. EHRs are built to share information with other health care providers and organizations—such as laboratories, specialists, medical imaging facilities, pharmacies, emergency facilities, and school and workplace clinics.

In the meantime, as discussed earlier, social determinants of health (SDOH) are the conditions in which people live that affect quality-of-life and health outcomes. Such SDOH include a wide range of conditions such as substance use, living situation, employment, education, racism, geography, pollution, and so on. SDOH may contribute ton decreased life expectancy. For example, substance abuse (including alcohol, drug, and tobacco use) is increasingly recognized as a key factor for morbidity and mortality; more people are living alone, leading to increased social isolation and negative health outcomes; employment and occupation impact income, societal status, hazards encountered, and health. Understanding SDOH, including behaviors influenced by these social factors, can inform clinical decision-making. SDOH are characterized in the EHR through structured data and unstructured clinical text; however, clinical text captures detailed descriptions of these determinants, beyond the representation in structured data. This text-encoded information must be automatically extracted for secondary use applications, like large-scale retrospective studies and clinical decision support systems. The automatically extracted data can augment the available structured data to create a more comprehensive patient representation in these downstream applications.

At least some aspects of the inventive concepts are directed to the extraction of SDOH information from history sections of clinical notes contained, for example, in EHRs. FIG. 1 illustrates an example of SDOH annotations in BRAT format, which was highlighted in a shared task of the 2022 National NLP Clinical Challenges (n2c2). The corpus used in the shared task contains annotated events for Social Determinant Event (SDE), where each social determinant event includes a trigger that anchors the event and one or more arguments that characterize the event. The arguments capture status, type, extent, and temporal information. FIG. 1 shows one example of SDE annotations in BRAT format. BRAT is tool for text annotation, i.e., for adding notes to existing text documents. It is designed in particular for "structured" annotation, where the notes are not freeform text but have a fixed form that can be automatically processed and interpreted by a computer.

In the example of FIG. 1, three lines or entries of clinical text are shown, namely, "SOCIAL HISTORY: Used to be a chef; currently unemployed", "Tobacco use: quit 7 years ago; 15-20 pack years", and "Alcohol use: no Drug use: no"

Several categories of BART annotations are also shown as well in the example of FIG. 1. "Text span" annotations are those, such as the boxes marked with "Tobacco", "Alcohol", "Drug", and so on. Another category illustrated in FIG. 1 is "relation" annotations, such as the "status" and "amount" relations in the example. BRAT also supports the annotation of "n-ary associations" that can link together any number of other annotations participating in specific roles. This category of annotation can be used for example for event annotation.

For descriptive purposes, the example of FIG. 1 will be referenced throughout the remainder of the detailed description that follows.

The inventive concepts provide a mechanism to automatically extract SDOH from clinical texts. Specifically, a sequence-to-structure generation model is utilized to directly extract all the SDOH in an end-to-end manner. The model is based on a transformer encoder-decoder architecture, where given a sequence of tokens is input, the encoder encodes the input into a sequence of token representations, and the decoder uses these representations and a greedy decoding algorithm to predict the outputs token-by-token.

Even though sequence to structure generation model of the embodiments is designed for extracting SDOH, it can be directly applied for other different information extraction tasks that involve the identification of trigger and argument spans, normalizing arguments, and predicting links between trigger and argument spans. In fact, such information extraction tasks are pervasive on almost any businesses that produce or rely on large volume of text data, for instance, de-identifying the patient information from electronic health record, extracting key issues from complaints data, standardizing radiology procedure descriptions, and so on.

Embodiments herein improve the SDOH extraction task, which provides a solution for more comprehensive patient representation, and can potentially improve patient safety. Such SDOH information is also beneficial to lots of downstream applications such as large-scale retrospective studies, cohort selection, clinical decision support systems, and so on. Further, embodiments herein atomically extract structural information from large volumes of text, which provide essential support for natural language understanding by recognizing and resolving concepts, entities, events described in text, and inferring the relations among them. Such automation processes can save time and money, and improve the productivity.

The inventive concepts are directed to a sequence-to-structure generation paradigm for event extraction, which can directly extract events from the text in an end-to-end manner. Specifically, instead of decomposing event structure prediction into different subtasks and predicting labels, embodiments herein uniformly model the whole event extraction process in a neural network-based sequence-to-structure architecture, and all triggers, arguments, and their labels are universally generated as natural language words. As an example, a subsequence "(Tobacco Tobacco Use)" is generated for trigger extraction, where both event type "Tobacco" and event trigger "Tobacco Use" are treated as natural language words. Compared with previous methods, the embodiments herein are more data-efficient. That is, the embodiments herein can be learned using only coarse parallel text-record annotations, i.e., pairs of sentences, event records, rather than fine-grained token-level annotations. In addition, the uniform architecture facilitates modeling, learning and exploiting the interactions between different underlying predictions, and the knowledge can be seamlessly shared and transferred between different components.

Figure 2:
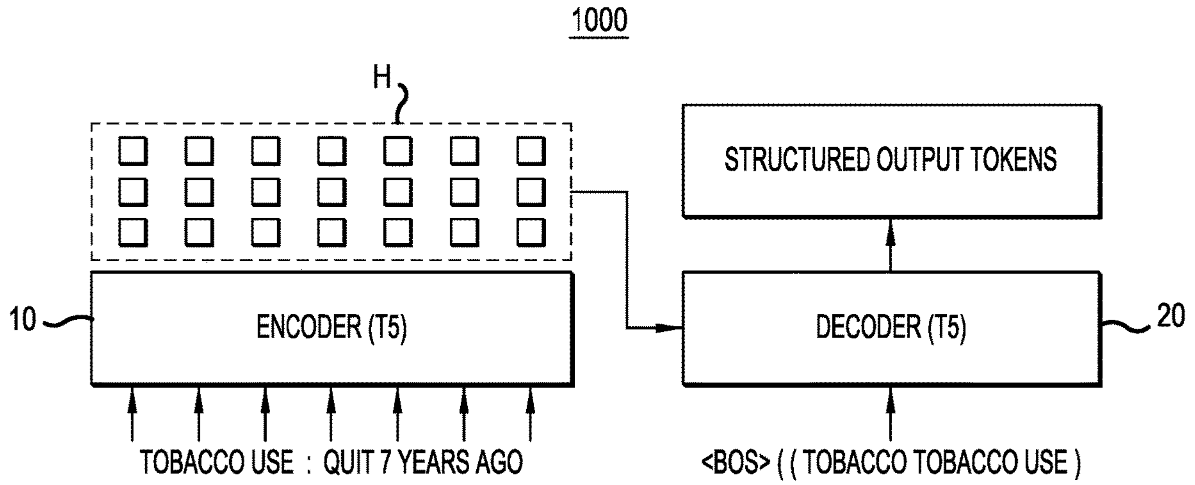
FIG. 2 is a block diagram illustrating the architecture of a sequence-to-structure model according to one or more embodiments of the inventive concepts.
Figure 3:
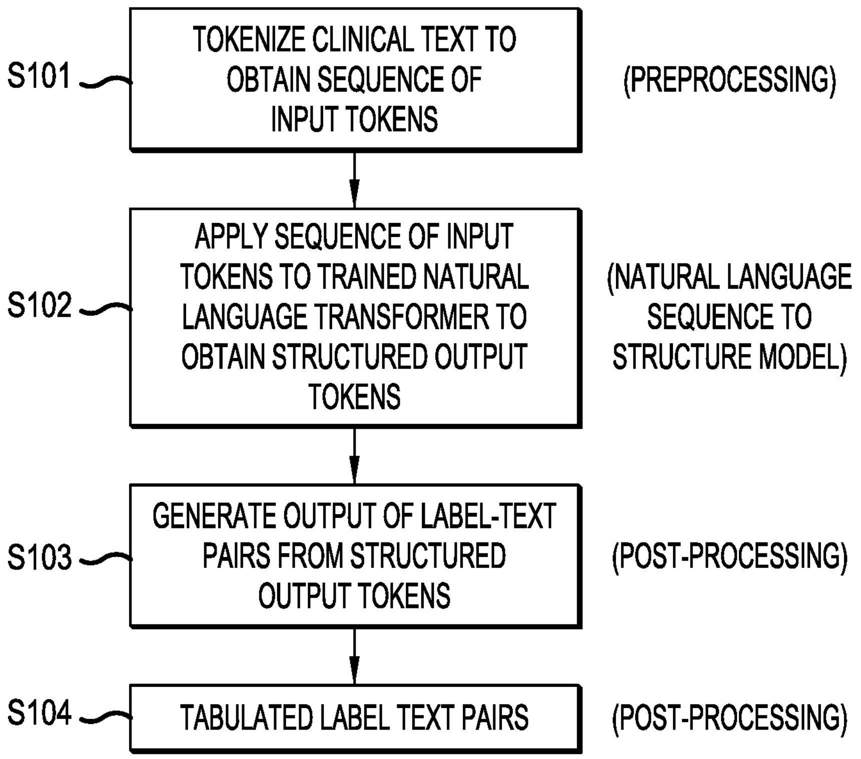
FIG. 3 is a flowchart for reference in describing the sequence to structure model according to one or more embodiments of the inventive concepts.
Figure 4:
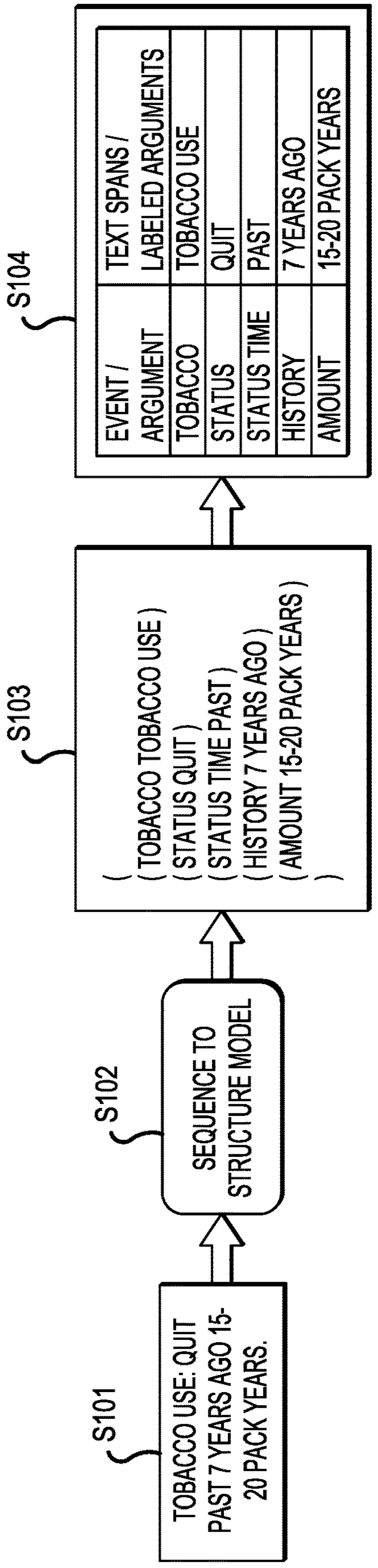
FIG. 4 adopts the example of FIG. 1 to provide an illustrative example of the generation of the ADE annotations for input text according to one or more embodiments of the inventive concepts.
Figure 5:
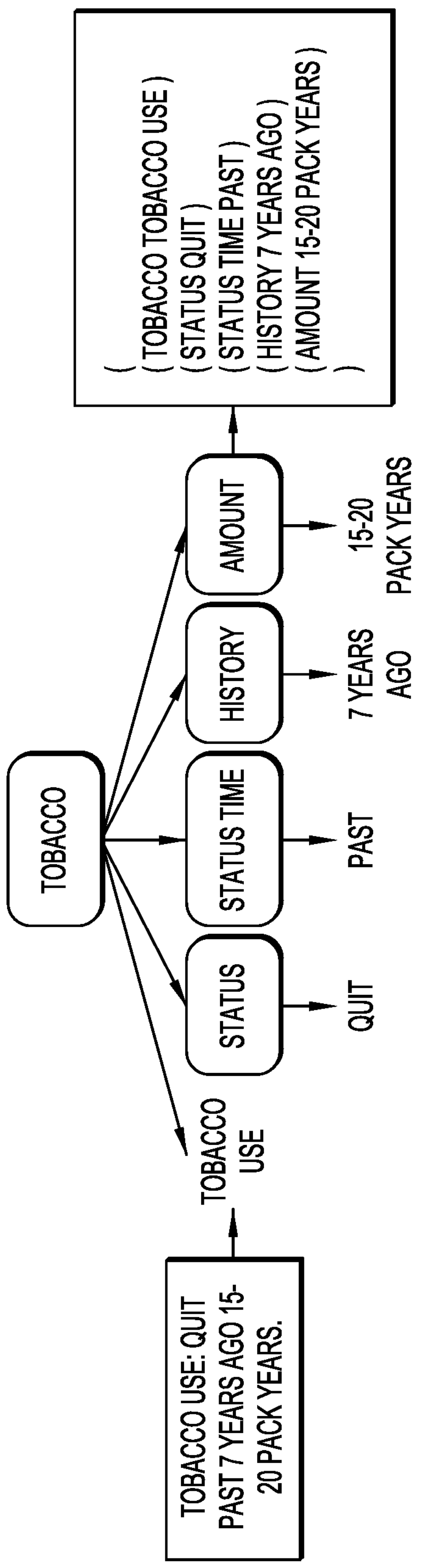
FIG. 5 is a diagram illustrating Event-based annotations (in tree structure and linearized format) for the input text according to one or more embodiments of the inventive concepts.

FIG. 2 is a block diagram illustrating the architecture of a sequence-to-structure model according to one or more embodiments of the inventive concepts. FIG. 3 is a flowchart for reference in describing the sequence to structure model according to one or more embodiments of the inventive concepts. FIG. 4 adopts the example of FIG. 1 to provide an illustrative example of the generation of the ADE (Adobe Digital Editions) annotations for input text according to one or more embodiments of the inventive concepts. FIG. 5 is a diagram illustrating Event-based annotations (in tree structure and linearized format) for the input text according to one or more embodiments of the inventive concepts.

Referring collectively to FIGS. 2-5, a pre-trained natural language model T5 transformer 1000 is adopted as a transformer-based encoder-decoder architecture. T5 is an example of a transformer based encoder-decoder model used for text generation developed by Google. As shown, the T5 transformer includes an encoder 10 and a decoder 20. The encoder H=Encoder(X) takes a sequence of words $X=\{x_0, x_1, \ldots, x_n\}$ as inputs, and generates a sequence of representations $H=\{h_0, h_1, \ldots, h_n\}$, and the decoder $y_t$=Decoder($y_{t-1}$, H) takes the sequence of representations H and the generated token $y_{t-1}$ at time step t-1 as input to generate one token at every time step, where $y_0$="G bus>".

At preprocessing step S101, clinical text is retrieved and preprocessed into a sequence of input tokens. As described above, the clinical text may be retrieved from the EHRs of one or more patients. Generally speaking, a tokenizer (not shown) converts the incoming text to a numerical data structure suitable for machine learning. In the given example, the clinical text is the sequence of words/punctuation: "Tobacco Use: quit & years ago 15-20 pack years."

At step S102, the sequence of input tokens are applied as inputs to the pre-trained T5 transformer 100. As described above, the encoder X generates a sequence of representations from the input tokens, and generates an output token based on the representations and a previous output token. The result is a sequence of structured output tokens. This constitutes the sequence to structure model of the embodiments.

At post-processing step S103, the generated output, which is the sequence of structured output tokens, are converted to text in which the text within the parentheses are label-text pairs.

At post-processing step S104, the label-text pairs are tabulated and output into a table format, such as shown by the table in FIG. 4.

A primary component of the embodiments is the sequence to structure model (FIG. 2 and step 102). The trained sequence to structure model that can generate SDEs given texts from social history section of clinical notes. Such a sequence to structure model could be any sequence-to-sequence models, e.g., RNN-based or transformer-based. The inventive concepts are not limited to the model itself, and instead encompass a generation-based approach to extract SDEs by generating event trigger and its arguments for a given text. To train the model, the inventive concepts use existing transformer-based sequence to sequence (seq2seq) architecture, initialize the seq2seq model with T5 checkpoint, and further train on collected input-output pairs. The event based SDOH annotations are converted into a linearized format (shown in FIG. 5) that is appropriate for the sequence to structure model. Specifically, the inventive concepts first parse the SDE annotations (FIG. 1) into an event tree, and then linearize the event tree using depth-first traversal to natural language words, where "(" and ")" are the structure indicators used to represent the semantic structure of linear expression. Each part of the structure captures the event type, attributes, and corresponding text spans and argument type.

During training, a clinical note may be segmented into sentences using an open-source tool SpaCy. For each sentence, corresponding SDE annotations are extracted and converted into the linearized format. The models may then be trained on the input sentences and their linearized SDE annotations. During inference, for each clinical note, the predictions of each sentence may be concatenated together, the offsets for all the generated text spans may be identified, and the outputs may be converted into a table format.

Figure 6:
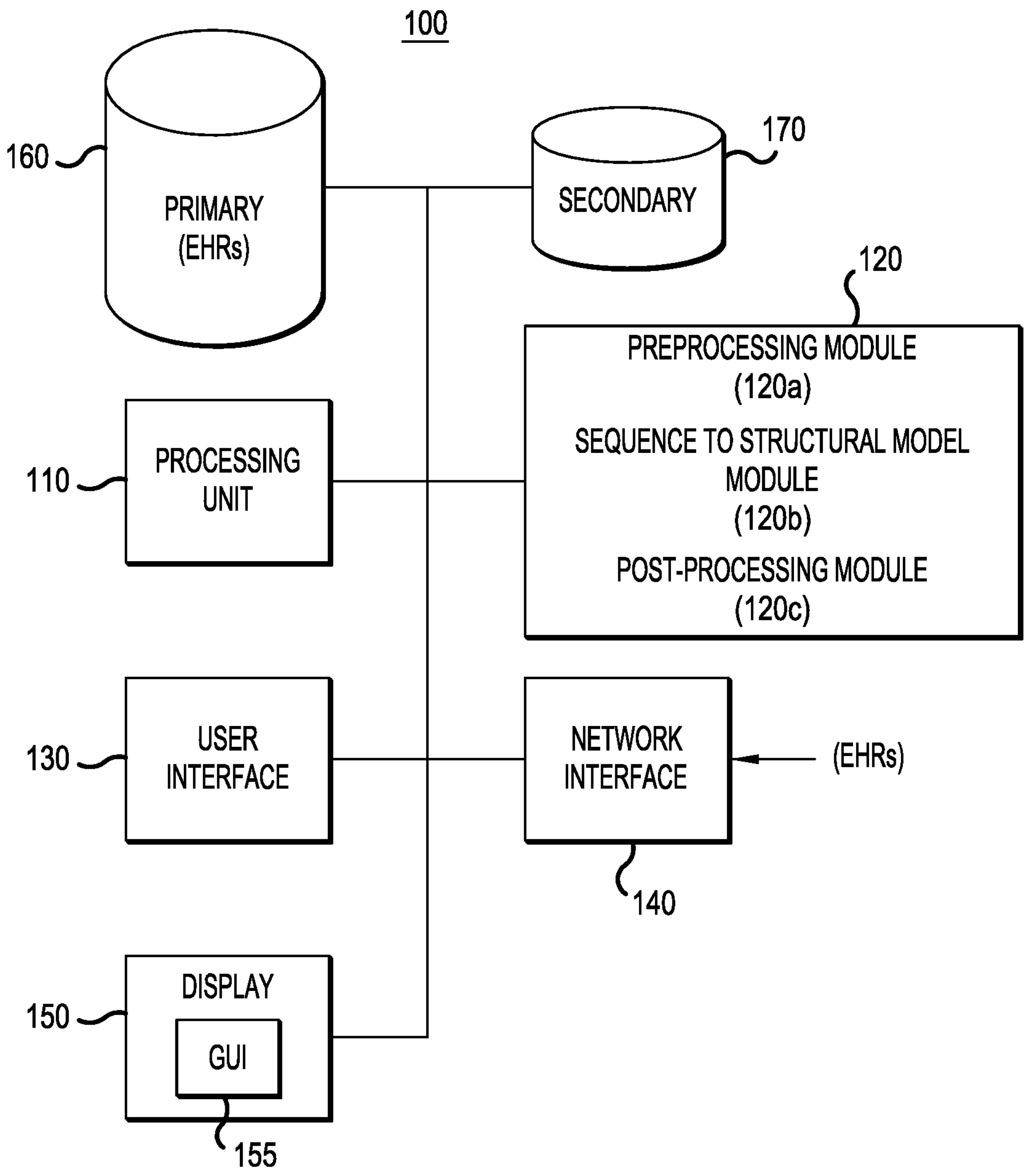
FIG. 6 is a simplified block diagram of a system for automatically extracting targeted medical information from clinical notes stored in memory, according to a representative embodiment.

FIG. 6 is a simplified block diagram of a system for automatically extracting targeted medical information from clinical notes stored in memory, according to a representative embodiment.

Referring to FIG. 6, system 100 includes a processing unit 110 and memory 120 for storing instructions executable by the processing unit 110 to implement processes described herein. In addition, the system 100 includes a user interface 130 for interfacing with a user, a network interface 140 for interfacing with other components and instruments, and a display 150, which may include graphical user interface (GUI) 155. The system 100 further includes or otherwise connects to primary data source 160 and a secondary data source 170, which is optional.

The processing unit 110 is representative of one or more processing devices, and is configured to execute software instructions to perform functions as described in the various embodiments herein. The processing unit 110 may be implemented by one or more servers, general purpose computers, central processing units, processors, microprocessors or microcontrollers, state machines, programmable logic devices, FPGAs, ASICs, or combinations thereof, using any combination of hardware, software, firmware, hard-wired logic circuits, or combinations thereof. As such, the term "processing unit" encompasses an electronic component able to execute a program or machine executable instructions, and may be interpreted to include more than one processor or processing core, as in a multi-core processor and/or parallel processors. The processing unit 110 may also incorporate a collection of processors within a single computer system or distributed among multiple computer systems, such as in a cloud-based or other multi-site application. Programs have software instructions performed by one or multiple processors that may be within the same computing device or which may be distributed across multiple computing devices.

The processing unit 110 may include an AI engine or module (e.g., a T5 transformer as described previously herein), which may be implemented as software that provides artificial intelligence, such as natural language processing (NLP) algorithms, and may apply machine learning, such as artificial neural network (ANN), convolutional neural network (CNN), or recurrent neural network (RNN) modeling, for example. The AI engine may reside in any of various components in addition to or other than the processing unit 110, such as the memory 120, an external server, and/or the cloud, for example. When the AI engine is implemented in a cloud, such as at a data center, for example, the AI engine may be connected to the processing unit 110 via the internet using one or more wired and/or wireless connection(s), e.g., via the network interface 140.

The memory 120 may include a main memory and/or a static memory, where such memories may communicate with each other and the processing unit 110 via one or more buses. The memory 120 stores instructions used to implement some or all aspects of methods and processes described herein, including the functions and methods described above with reference to FIGS. 2-5, for example. The memory 120 may include software modules. In embodiments of the inventive concepts, the memory 120 includes a preprocessing module 120*a* for executing the preprocessing tasks described above, a sequence to structure model module 120*b* for the executing the sequence to structure model describe above, and a post-processing module 120*c* for executing the post-processing tasks described above.

The memory 120 may be implemented by any number, type and combination of random access memory (RAM) and read-only memory (ROM), for example, and may store various types of information, such as software algorithms, data based models including ANNs, CNNs, RNNs, and other neural network based models, and computer programs, all of which are executable by the processing unit 110. The various types of ROM and RAM may include any number, type and combination of computer readable storage media, such as a disk drive, flash memory, an electrically programmable read-only memory (EPROM), an electrically erasable and programmable read only memory (EEPROM), registers, a hard disk, a removable disk, tape, compact disk read only memory (CD-ROM), digital versatile disk (DVD), floppy disk, blu-ray disk, a universal serial bus (USB) drive, or any other form of computer readable storage medium known in the art.

The memory 120 is a tangible storage medium for storing data and executable software instructions, and is non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A non-transitory storage medium is defined to be any medium that constitutes patentable subject matter under 35 U.S.C. § 101 and excludes any medium that does not constitute patentable subject matter under 35 U.S.C. § 101.

The memory 120 may store software instructions and/or computer readable code that enable performance of various functions. The memory 120 may be secure and/or encrypted, or unsecure and/or unencrypted.

The user interface 130 provides information and data output by the processing unit 110 to the user and/or receives information and data input by the user. That is, the user interface 130 enables the user to enter data and to control or manipulate aspects of the processes described herein, and also enables the processing unit 110 to indicate the effects of the user's control or manipulation. All or a portion of the user interface 130 may be implemented by the GUI 155, viewable on the display 150. The user interface 130 may include a mouse, a keyboard, a trackball, a joystick, a haptic device, a touchpad, a touchscreen, and/or voice or gesture recognition captured by a microphone or video camera, for example, or any other peripheral or control to permit user feedback from and interaction with the processing unit 110. The display 150 may be a monitor such as a computer monitor, a television, a liquid crystal display (LCD), an organic light emitting diode (OLED), a flat panel display, a solid-state display, or a cathode ray tube (CRT) display, or an electronic whiteboard, for example.

The network interface 140 provides information and data output by the processing unit 110 to other components and/or instruments, e.g., that require one or more of the clock output signals. The network interface 140 may include one or more of ports, drives, or other types of interconnect and/or transceiver circuitry. Optionally, the clinical text (EHRs) may be accessed over the network interface 140.

The primary data source 160 may include the EHRs retrieved over the network interface 140, for example. The secondary data source 170 may be included to make the workflow and performance analysis more complete.

For purposes of explanation, the memory 120 is described as including modules, each of which includes the machine executable instructions (e.g., in software or computer programs) corresponding to an associated capability of the system 100.

While the above-described embodiments can be applied to the extraction of SDOH information from clinical notes, the embodiments can also be applied in other information extraction tasks that that involve the identification of trigger and argument spans, normalizing arguments, and predicting links between trigger and argument spans.

In various embodiments where components, systems and/or methods are implemented using a programmable device, such as a computer-based system or programmable logic, it should be appreciated that the above-described systems and methods can be implemented using any of various known or later developed programming languages, such as "C", "C++ ", "C#", "Java", "Python", and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A computer-implemented method for improving accuracy and efficiency of extracting targeted structured medical information from unstructured clinical notes stored in memory, comprising:

retrieving from the memory a sequence of clinical texts of electronic health records, the clinical texts comprising unstructured clinical notes, wherein the clinical texts comprise a plurality of medical events;

tokenizing the sequence of the clinical texts to obtain a sequence of input tokens;

transforming, using a trained natural language based transformer, the sequence of input tokens into a sequence of structured output tokens, wherein the trained natural language based transformer comprises: (i) an encoder that receives the sequence of input tokens as inputs, and generates a sequence of representations; and (ii) a decoder that receives the sequence of representations and generates a sequence of structured output tokens, wherein, for each medical event of the plurality of medical events, the decoder identifies a trigger for the medical event in the clinical texts and predicts one or more associations between the identified trigger and at least one argument span characterizing the trigger in the clinical texts based on the sequence of representations; and post-processing the structured output tokens to obtain annotated text-label pairs of the clinical texts.

2. The computer-implemented method of claim 1, wherein the trained natural language based transformer is a T5 transformer.

3. The computer-implemented method of claim 2, wherein the decoder receives the sequence of representations and a previously generated token as inputs to generate one output token at each time step.

4. The computer-implemented method of claim 1, wherein the post-processing further includes converting the text-label pairs into a table format.

5. The computer-implemented method of claim 1, wherein the targeted medical information is social determinants of health (SDOH) information.

6. The computer-implemented method of claim 1, further comprising training the natural language based transformer to generate a sequence of structured output tokens from a sequence of input tokens, comprising generating event-based annotations from training clinical texts comprising a plurality of input sentences to create an event tree comprising the event-based annotations, linearizing the event tree, and training the natural language based transformer with the plurality of input sentences and the corresponding linearized event tree.

7. A system for improving accuracy and efficiency of extracting targeted structured medical information from unstructured clinical notes stored in memory, comprising a processor configured to:

retrieve from the memory a sequence of clinical texts of electronic health records, the clinical texts comprising unstructured clinical notes, wherein the clinical texts comprise a plurality of medical events;

tokenize the sequence of the clinical texts to obtain a sequence of input tokens;

transform, using a trained natural language based transformer, the sequence of input tokens into a sequence of structured output tokens, wherein the trained natural language based transformer comprises: (i) an encoder that receives the sequence of input tokens as inputs, and generates a sequence of representations; and (ii) a decoder that receives the sequence of representations and generates a sequence of structured output tokens, wherein, for each medical event of the plurality of medical events, the decoder identifies a trigger for the medical event in the clinical texts and predicts one or more associations between the identified trigger and at least one argument span characterizing the trigger in the clinical texts based on the sequence of representations; and obtain annotated text-label pairs of the clinical texts from the structure output tokens.

8. The system of claim 7, wherein the trained natural language based transformer is a T5 transformer.

9. The system of claim 8, wherein the decoder receives the sequence of representations and a previously generated token as inputs to generate one output token at each time step.

10. The system of claim 7, wherein the processor is further configured to convert the text-label pairs into a table format.

11. The system of claim 7, wherein the targeted medical information is social determinants of health (SDOH) information.

12. The system of claim 7, wherein the processor is further configured to train the natural language based transformer to generate a sequence of structured output tokens from a sequence of input tokens, comprising generating event-based annotations from training clinical texts comprising a plurality of input sentences to create an event tree comprising the event-based annotations, linearizing the event tree, and training the natural language based transformer with the plurality of input sentences and the corresponding linearized event tree.

13. A non-transitory computer-readable storage medium encoded with instructions which, when executed by a processor, cause the processor to:

retrieve from the memory a sequence of clinical texts of electronic health records, the clinical texts comprising unstructured clinical notes, wherein the clinical texts comprise a plurality of medical events;

tokenize the sequence of the clinical texts to obtain a sequence of input tokens;

transform, using a trained natural language based transformer, the sequence of input tokens into a sequence of structured output tokens, wherein the trained natural language based transformer comprises: (i) an encoder that receives the sequence of input tokens as inputs, and generates a sequence of representations; and (ii) a decoder that receives the sequence of representations and generates a sequence of structured output tokens, wherein, for each medical event of the plurality of medical events, the decoder identifies a trigger for the medical event in the clinical texts and predicts one or more associations between the identified trigger and at least one argument span characterizing the trigger in the clinical texts based on the sequence of representations;

obtain annotated text-label pairs of the clinical texts from the structure output tokens; and convert the text-label pairs of the clinical texts into a structured table format; and display the structured table of text-label pairs of the clinical text.

14. The non-transitory computer-readable storage medium of claim 13, wherein the trained natural language based transformer is a T5 transformer.

15. The non-transitory computer-readable storage medium of claim 13, wherein the decoder receives the sequence of representations and a previously generated token as inputs to generate one output token at each time step.

16. The non-transitory computer-readable storage medium of claim 13, further comprising training the natural language based transformer to generate a sequence of structured output tokens from a sequence of input tokens, comprising generating event-based annotations from training clinical texts comprising a plurality of input sentences to create an event tree comprising the event-based annotations, linearizing the event tree, and training the natural language based transformer with the plurality of input sentences and the corresponding linearized event tree.

* * * * *